United States Patent [19]

Regel et al.

[11] 4,238,498
[45] Dec. 9, 1980

[54] ANTIMYCOTIC SUBSTITUTED DIPHENYL-IMIDAZOLYL-METHANES

[75] Inventors: Erik Regel; Karl H. Büchel; Wilfried Draber; Manfred Plempel; Ingo Haller, all of Wuppertal, Fed. Rep. of Germany

[73] Assignee: Bayer Aktiengesellschaft, Leverkusen, Fed. Rep. of Germany

[21] Appl. No.: 8,632

[22] Filed: Feb. 1, 1979

[30] Foreign Application Priority Data

Feb. 24, 1978 [DE] Fed. Rep. of Germany ....... 2808086

[51] Int. Cl.³ ................. A61K 31/415; C07D 233/58; C07D 233/56
[52] U.S. Cl. ............................... 424/273 R; 548/345; 568/809
[58] Field of Search ..................... 548/345; 424/273 R

[56] References Cited

U.S. PATENT DOCUMENTS

| 3,769,422 | 10/1973 | Timmler et al. | 424/273 R |
| 3,836,540 | 9/1974 | Stelt | 548/345 |
| 4,118,487 | 10/1978 | Regel et al. | 548/345 |

FOREIGN PATENT DOCUMENTS 2418502 10/1975 Fed. Rep. of Germany .

Primary Examiner—Alan L. Rotman
Assistant Examiner—Natalia Harkaway
Attorney, Agent, or Firm—Sprung, Felfe, Horn, Lynch & Kramer

[57] ABSTRACT

The invention provides a series of substituted diphenyl-imidazolyl-methanes useful as antimycotic agents. Also included in the invention are pharmaceutical compositions containing said diphenyl-imidazolyl-methanes and methods for the use of said compounds and compositions. The invention additionally includes methods for the manufacture of the diphenyl-imidazolyl-methanes.

17 Claims, No Drawings

ANTIMYCOTIC SUBSTITUTED DIPHENYL-IMIDAZOLYL-METHANES

The present invention relates to certain new substituted diphenyl-imidazolyl-methanes, to a process for their production and to their use as antimycotic agents.

It has already been disclosed that biphenylimidazolyl-methane derivatives display a good antimycotic action (compare DT-OS (German Published Specification) No. 2,418,502 and DT-OS (German Published Specification) No. 2,461,406). However, their action is not always completely satisfactory on all species of fungi. Furthermore, it is already known that 2-chlorophenyl-imidazol-1-yl-naphth-1-yl-methane has antimycotic properties (compare J. Pharm. Sci. 62, 773 to 778 (1973)). Its action, however, is also not always completely satisfactory, especially against blastomyces and moulds.

According to the present invention, there are provided compounds which are substituted diphenyl-imidazolylmethanes of the general formula

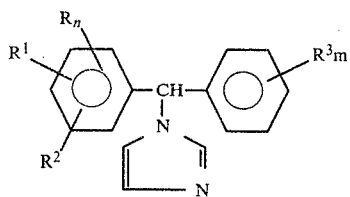

(I)

or a salt thereof, in which
R denotes a halogen atom or an alkyl, alkoxy or halogenoalkyl group,
$R^1$ denotes an optionally substituted cycloalkyl group,
$R^2$ denotes a hydrogen atom, or
$R^1$ and $R^2$, in the ortho-position relative to each other, together denote an optionally substituted multi-membered methylene bridge,
$R^3$ denotes a halogen atom or an alkyl, halogenoalkyl, alkoxy, alkylthio, alkylsulphonyl, amino, nitro or cyano group and
n and m are independently 0, 1, 2 or 3.
They display powerful antimycotic properties.

The present invention further provides a process for the production of compounds of the present invention, in which a diphenyl-halogeno-methane of the general formula

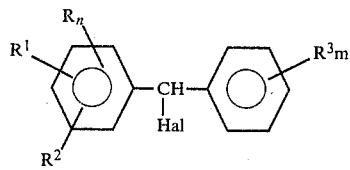

(II)

in which R, $R^1$, $R^2$, $R^3$, m and n have the meaning indicated above and Hal denotes a halogen atom, is reacted with imidazole, if appropriate in the presence of an acid-binding agent and if appropriate in the presence of a diluent.

In some cases it is advantageous to employ the silver salt or alkali metal salt, such as the sodium salt or potassium salt, instead of the imidazole.

Furthermore, the diphenyl-imidazolyl-methanes obtainable according to the invention can be converted into salts by reaction with acids.

Surprisingly, the diphenyl-imidazolyl-methanes according to the invention exhibit a better and broader antimycotic, therapeutically usable activity than the biphenyl-imidazolyl-methane derivatives known from the state of the art and than the known compound 2-chlorophenylimidazol-1-yl-naphth-1-yl-methane, which are very closely related compounds chemically and from the point of view of their action. The active compounds according to the invention thus represent a valuable advance in pharmacy.

If 2-chlorophenyl-indan-5-yl-chloromethane and imidazole are used as starting substances, the course of the reaction can be represented by the equation which follows:

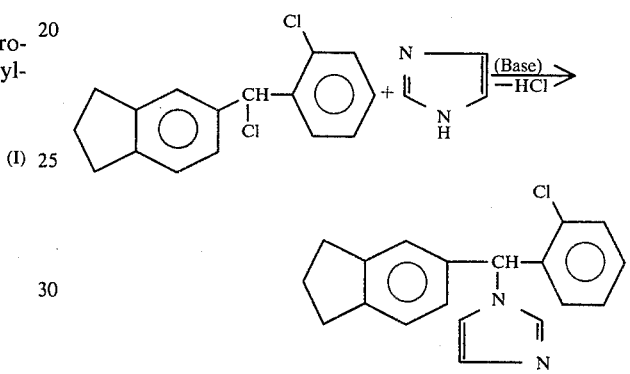

The radicals in the new compounds of the present invention of Formula I and in the starting compounds of formula (II) have the following preferred meanings.

R preferably represents halogen, in particular fluorine, chlorine and bromine, straight-chain or branched alkyl or alkoxy with in each case 1 to 4 carbon atoms and halogenoalkyl with 1 to 4 carbon atoms and up to 5 halogen atoms, in particular with 1 or 2 carbon atoms and up to 3 identical or different halogen atoms, halogen atoms being, in particular, fluorine and chlorine, and trifluoromethyl being mentioned as an example. $R^1$ preferably represents cycloalkyl with 3 to 7 carbon atoms which is optionally monosubstituted or polysubstituted, preferred substituents being: Halogen, in particular fluorine, chlorine or bromine, and alkyl with 1 to 4 carbon atoms. $R^2$ preferably represents hydrogen and, together with $R^1$, in the ortho-position relative to one another, a methylene bridge with 3 to 5 methylene groups which is optionally monosubstituted or polysubstituted, preferred substituents which may be mentioned being: halogen, in particular fluorine, chlorine or bromine, and alkyl with 1 to 4 carbon atoms. $R^3$ preferably represents halogen, in particular fluorine, chlorine or bromine, straight-chain or branched alkyl with 1 to 4 carbon atoms, halogenoalkyl with 1 to 4 carbon atoms and up to 5 halogen atoms, in particular with 1 or 2 carbon atoms and up to 3 identical or different halogen atoms, halogen atoms being, in particular, fluorine and chlorine, and trifluoromethyl being mentioned as an example, and furthermore, preferably, alkoxy, alkylthio and alkylsulphonyl with in each case 1 to 4, in particular 1 to 2, carbon atoms, and the amino, nitro and cyano group.

Hal preferably represents a chlorine or fluorine atom.

The diphenyl-halogeno-methanes of the formula (II) to be used as starting substances are not yet known. However, they can be obtained by customary methods by halogenating carbinols of the formula

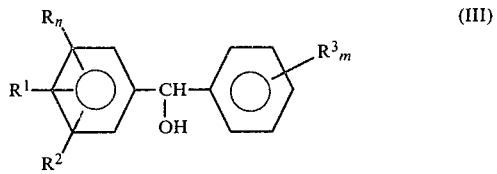

in which R, $R^1$, $R^2$, $R^3$, m and n have the meaning indicated above, in a known manner, such as, for example, with hydrogen chloride (in this context, compare J. Org. Chem. 36, (18), 2724 (1971)) or with thionyl chloride (in this context, compare Izv. Akad.SSSR 10, 1804 (1962) and the preparation examples).

The carbinols of the formula (III) are likewise not yet known, but they can be prepared by customary methods. They are obtained, for example, by reducing with aluminium isopropylate the ketones obtained by a Friedel-Crafts reaction (in this context, compare Izv..Akad.SSSR 10, 1804 (1962), Ž.obšč.Chim. 34, (3), 977 (1964) and Ž.org.Chim. 2, (7), 1288 (1966)). However, it is also possible to carry out the reduction with any other reducing agent, such as, for example, sodium borohydride (in this context, compare the preparation examples).

Preferred possible diluents for the reaction according to the invention are inert organic solvents. These include, preferably, ketones, preferably dialkyl ketones having up to 4 carbon atoms such as diethyl ketone, and in particular acetone and methyl ethyl ketone; nitriles, such as propionitrile, and in particular acetonitrile; alcohols, particularly alkanols having up to 4 carbon atoms such as ethanol or isopropanol; ethers, such as tetrahydrofurane or dioxane; aromatic hydrocarbons, such as benzene, toluene and halogenated aromatic hydrocarbons, such as dichlorobenzene; formamides, such as, in particular, dimethylformamide and diethylformamide, and halogenated hydrocarbons, e.g. halogenated alkanes, such as methylene chloride, ethylene chloride, carbon tetrachloride or chloroform.

If the reaction according to the invention is carried out in the presence of an acid-binding agent, it is possible to add any of the inorganic or organic acid-binding agents which can customarily be used, such as alkali metal carbonates, for example sodium carbonate and potassium carbonate, and sodium bicarbonate, or such as lower tertiary alkylamines, cycloalkylamines or aralkylamines, for example triethylamine, N,N-dimethylcyclohexylamine, dicyclohexylmethylamine and N,N-dimethylbenzylamine, and furthermore pyridine and diazabicyclooctane. An excess of imidazole is preferably used.

The reaction temperatures can be varied within a substantial range. In general, the reaction is carried out between about 30° and about 200° C., preferably at the boiling point of the solvent.

In carrying out the process according to the invention, 1 to 2.5 mols of imidazole and 1 to 2.5 mols of acid-binding agent are preferably employed per 1 mol of the compounds of the formula (II). In order to isolate the compounds of the formula (I), the solvent is distilled off, the residue is taken up in an organic solvent and the mixture is washed with water. The organic phase is dried over sodium sulphate and freed from solvent in vacuo. If appropriate, the residue is purified by distillation, recrystallisation or chromatography.

All the physiologically acceptable acids can be used for the preparation of acid addition salts of the compounds of the formula (I). These acids include, preferably, hydrogen halide acids, such as, for example, hydrochloric acid and hydrobromic acid, especially hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Examples which may be mentioned of particularly active representatives of the active compounds according to the invention, in addition to the preparation examples and the examples in Table 1, are: 4-cyclopropylphenyl-2-fluorophenyl-imidazol-1-yl-methane, 4-cyclohexylphenyl-4-chlorophenyl-imidazol-1-yl-methane, 4-cyclohexylphenyl-4-fluorophenyl-imidazol-1-yl-methane, 4-cyclohexylphenyl-2-fluorophenyl-imidazol-1-yl-methane, 4-cyclohexylphenyl-2,4-dichlorophenyl-imidazol-1-yl-methane, 4-chloro-3-cyclohexylphenyl-2-chlorophenyl-imidazol-1-yl-methane, 4-chloro-3-cyclohexylphenyl-4-chlorophenyl-imidazol-1-yl-methane, 4-chloro-3-cyclohexylphenyl-2-fluorophenyl-imidazol-1-yl-methane, 4-chloro-3-cyclohexylphenyl-4-fluorophenyl-imidazol-1-yl-methane, 4-chloro-3-cyclohexylphenyl-2,4-dichlorophenyl-imidazol-1-yl-methane, 4-(3-bromocyclohexyl)-phenyl-2-chlorophenyl-imidazol-1-yl-methane, 4-(3-bromocyclohexyl)-phenyl-4-chlorophenyl-imidazol-1-yl-methane, 4-(3-bromocyclohexyl)-phenyl-2-fluorophenyl-imidazol-1-yl-methane, 4-(3-bromocyclohexyl)-phenyl-4-fluorophenyl-imidazol-1-yl-methane, 4-(3-bromocyclohexyl)-phenyl-2,4-dichlorophenyl-imidazol-1-yl-methane, 4-cyclopentyl-2-methylphenyl-phenyl-imidazol-1-yl-methane, 4-cyclopentyl-2-methylphenyl-2-chlorophenyl-imidazol-1-yl-methane, 4-cyclopentyl-2-methylphenyl-4-chlorophenyl-imidazol-1-yl-methane, 4-cyclopentyl-2-methylphenyl-2-fluorophenyl-imidazol-1-yl-methane, 4-cyclopentyl-2-methylphenyl-4-fluorophenyl-imidazol-1-yl-methane, 4-cyclopentyl-2-methylphenyl-2,4-dichlorophenyl-imidazol-1-yl-methane, 4-(1-methylcyclohexyl)-phenyl-2-chlorophenyl-imidazol-1-yl-methane, 4-(1-methylcyclohexyl)-phenyl-4-chlorophenyl-imidazol-1-yl-methane, 4-(1-methylcyclohexyl)-phenyl-2-fluorophenyl-imidazol-1-yl-methane, 4-(1-methylcyclohexyl)-phenyl-4-fluorophenyl-imidazol-1-yl-methane, 4-(1-methylcyclohexyl)-phenyl-2,4-dichlorophenylimidazol-1-yl-methane, 6-chloro-1,2,3,4-tetrahydro-naphth-7-yl-phenyl-imidazol-1-yl-methane, 6-chloro-1,2,3,4-tetrahydro-naphth-7-yl-2-chlorophenyl-imidazol-1-yl-methane, 6-chloro-1,2,3,4-tetrahydro-naphth-7-yl-2-fluorophenyl-imidazol-1-yl-methane, 5-chloro-1,2,3,4-tetrahydronaphth-8-yl-phenyl-imidazol-1-yl-methane, 5-chloro-1,2,3,4-tetrahydro-naphth-8-yl-2-chlorophenyl-imidazol-1-yl-methane, 5-chloro-1,2,3,4-tetrahydro-naphth-8-yl-2-bromophenyl-imidazol-1-yl-methane, 2-chloro-1,2,3,4-tetrahydro-naphth-6-yl-phenyl-imidazol-1-yl-methane, 2-chloro-1,2,3,4-tetrahydro-naphth-6-yl-2-chlorophenyl-imidazol-1-yl-methane, 2-chloro-1,2,3,4-tetrahydro-naphth-6-yl-2-fluorophenyl-imidazol-1-yl-methane, 1,2,3,4-tetrachloro-1,2,3,4-tetrahydro-naphth- 6-yl-phenyl-imidazol-1-yl-methane, 1,2,3,4-tetrachloro-1,2,3,4-tetrahydro-naphth-6-yl-2-chlorophenyl-imidazol-1-yl-methane, 1,2,3,4-tetrachloro-1,2,3,4-tetrahydro-naphth-6-yl-2-fluorophenyl-imidazol-1-yl-methane, 1,2,3,4-tetrachloro-1,2,3,4-tetrahydro-naphth-6-yl-4-chlorophenyl-imidazol-1-yl-methane, 5-methyl-1,2,3,4-tetrahydro-naphth-7-yl-phenyl-imidazol-1-yl-methane, 5-methyl-1,2,3,4-tetrahydro-naphth-7-yl-2-chlorophenyl-imidazol-1-yl-methane, 5-methyl-1,2,3,4-tetrahydro-naphth-7-yl-2-fluorophenyl-imidazol-1-yl-methane, 5-methyl-1,2,3,4-tetrahydro-naphth-7-yl-2-methylphenyl-imidazol-1-yl-methane, 5-methyl-1,2,3,4-tetrahydro-naphth-7-yl-2,6-difluorophenyl-imidazol-1-yl-methane, 3,4-pentamethylenephenyl-phenyl-imidazol-1-yl-methane, 3,4-pentamethylenephenyl-2-chlorophenyl-imidazol-1-yl-methane, 3,4-pentamethylenephenyl-2-fluorophenyl-imidazol-1-yl-methane, indan-4-yl-phenyl-imidazol-1-yl-methane, indan-4-yl-2-chlorophenyl-imidazol-1-yl-methane, indan-4-yl-2-fluorophenyl-imidazol-1-yl-methane, indan-4-yl-2-bromophenyl-imidazol-1-yl-methane, indan-4-yl-2-methylphenyl-imidazol-1-yl-methane, indan-4-yl-2,3-dimethylphenyl-imidazol-1-yl-methane, indan-5-yl-2-bromophenyl-imidazol-1-yl-methane, 3-chloro-indan-5-yl-phenyl-imidazol-1-yl-methane, 3-chloro-indan-5-yl-2-chlorophenyl-imidazol-1-yl-methane, 3-chloro-indan-5-yl-4-chlorophenyl-imidazol-1-yl-methane, 3-chloro-indan-5-yl-2-fluorophenyl-imidazol-1-yl-methane, 6-chloro-indan-5-yl-phenyl-imidazol-1-yl-methane, 6-chloro-indan-5-yl-2-chlorophenyl-imidazol-1-yl-methane, 6-chloro-indan-5-yl-2-fluorophenyl-imidazol-1-yl-methane, 3-methyl-indan-5-yl-phenyl-imidazol-1-yl-methane, 3-methyl-indan-5-yl-2-chlorophenyl-imidazol-1-yl-methane and 3-methyl-indan-5-yl-2-fluorophenyl-imidazol-1-yl-methane.

The compounds of the formula (I) which can be used according to the invention, and their salts display powerful antimicrobial actions, in particular powerful antimycotic actions. They possess a very broad antimycotic action spectrum, especially against dermatophytes and blastomyces as well as biphase fungi, for example against varieties of Candida, such as *Candida albicans*, varieties of Epidermphyton, such as *Epidermophyton floccosum*, varieties of Aspergillus, such as *Aspergillus niger* and *Aspergillus fumigatus*, varieties of Trichophyton, such as *Trichophyton mentagrophytes*, varieties of Microsporon, such as *Microsporon felineum* and varieties of Penicillium, such as *Penicillium commune*. The listing of these micro-organisms in no way implies a limitation of the germs which can be combated but is only of illustrative character.

Examples which may be mentioned of fields of indication in medicine are: dermatomycoses and systemic mycoses caused by *Trichophyton mentagrophytes* and other varieties of Trichophyton, varieties of Microsporon, *Epidermophyton floccosum*, blastomyces and biphase fungi as well as moulds.

The present invention provides pharmaceutical compositions containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatin and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contan colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments any include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, in particular intravenously. Preferred pharmaceutical compositions and medicaments are therefore those adapted for administration such as parenteral administration. Administration in the method of the invention is preferably parenteral administration.

In general it has proved advantageous to administer amounts of from 10 mg to 300 mg/kg, preferably 50 mg to 200 mg/kg, of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use lens than the above-mentioned minimum dosage rate, whilst other cases the upper limit mentioned must be exceeded to achieve the desired results. Where larger amounts are administered it can be advisable to divide these into several individual administrations over the course of the day.

The following Examples A and B illustrate the antimicrobial activity of the compounds used in the invention.

EXAMPLE A

Antimycotic in vitro activity

Description of the experiment

The in vitro tests were carried out in a series dilution test with germ inocula of an average of $5 \times 10^4$ germs/ml of substrate. The nutrient medium as (a) for dermatophytes and moulds: Sabouraud's milieu d'épreuve and (b) for yeasts: meat extract/glucose broth.

The incubation temperature was 28° C. and the duration of incubation was 24 to 96 hours.

In these in vitro tests, for example, the compounds, according to the invention, of Examples 1, 2, 3, 4, 5, 6, 7, 8, 9 and 10 exhibit good antimycotic properties which are superior to those of the compounds known from the prior art.

EXAMPLE B

Antimycotic in vivo activity (local), using experimental trichophytosis of guineapigs as a model

Description of the experiment

White guineapigs of the Pirbright white strain were infected, on their shaven, non-scarified backs, with a micronidia and macroconidia suspension of Trichophyton mentagrophytes. In the case of untreated animals, the typical pattern of dermantophytosis develops within 12 days after infection, with reddening, scaling and loss of hair up to total integumentary defect at the point of infection. The treated animals were treated locally once a day, starting with the 3rd. day after infection, with 1% strength solutions of the comparison formulations and the formulations according to the invention in polyethylene glycol.

On the 14th. day after infection, the untreated control animals and the animals treated with the comparison active compounds exhibited the typical pattern of dermatophytosis, whilst the formulations to be tested had inhibited the course of the infection.

The experiments thus carried out show, for example, the good antimycotic in vivo activity of the compounds, according to the invention, of Examples 4, 6, 7, 9 and 10. The following Examples illustrate the preparation of the compounds of the invention.

EXAMPLE 1

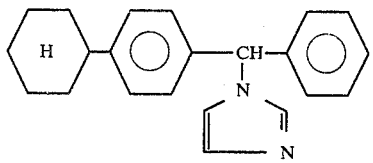

37 g (0.13 mol) of 4-cyclohexylbenzhydryl chloride are introduced in portions into a suspension of 44.3 g (0.65 mol) of imidazole in 100 ml of 1,2-dichlorobenzene at 170° C. After stirring the reaction mixture at 170° C. for one hour, it is evaporated at 80° to 90° C. on a rotary evaporator and the residue is dissolved in methylene chloride. After washing the organic phase several times with water, the methylene chloride solution is dried over sodium sulphate and evaporated. The oil which remains is extracted with petroleum ether, the petroleum ether solution is evaporated and the oil which results if purified by chromatography (absorbent: silica gel 60, Merck; solvent mixture: chloroform: methanol=20:1).

21.7 g (53% of theory) of 4-cyclohexylphenyl-imidazol-1-yl-phenyl-methane of refractive index $n_D^{20}=1.5831$ are obtained.

Preparation of the starting materials

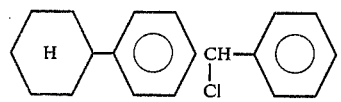

76 g (0.286 mol) of 4-cyclohexylphenylphenylcarbinol are introduced in portions into a mixture of 143 ml (2 mols) of thionyl chloride and 200 ml of benzene at 70° C. The reaction mixture is heated to 70° C. for 15 hours and then evaporated. The oil which remains is stirred with petroleum ether, whereupon it solidifies to a crystal sludge. 79 g (96% of theory) of 4-cyclohexylphenyl-phenylchloromethane of melting point 75° C. are obtained.

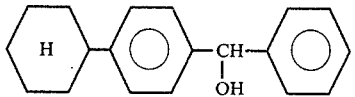

6.4 g (0.17 mol) of sodium boranoate are introduced in portions into a solution of 92.5 g (0.35 mol) of 4-cyclohexylbenzophenone in 300 ml of ethyl alcohol. The reaction mixture is heated under reflux for 15 hours and then poured onto ice. The organic phase is taken up in methylene chloride, the methylene chloride phase is washed with water until neutral, dried over sodium sulphate and filtered and the filtrate is evaporated. After triturating with petroleum ether, 77.3 g (83% of theory) of 4-cyclohexylphenyl-phenylcarbinol of melting point 79° C. are obtained.

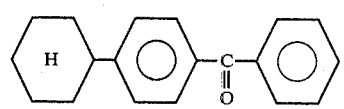

67 g (0.5 mol) of aluminium chloride are added in portions to a mixture of 80 g (0.5 mol) of cyclohexylbenzene 70 g (0.5 mol) of benzoyl chloride and 500 ml of methylene chloride at room temperature. After 15 hours, the reaction mixture is poured onto ice/hydrochloric acid. The organic phase is washed with water until neutral, dried over sodium sulphate and evaporated. The crude product is purified by distillation. 93.3 g (75% of theory) of 4-cyclohexylbenzophenone of boiling point 160° to 175° C./$_{0.1}$ mm are obtained.

EXAMPLE 2

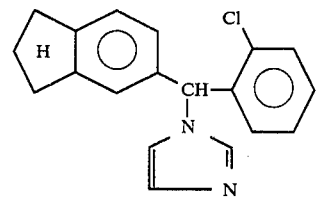

71 g (0.25 mol) of 2-chlorophenyl-indan-5-yl-chloromethane are introduced in portions into a suspension of 85 g (1.25 mols) of imidazole in 200 ml of 1,2-dichlorophenol at 180° C. After stirring the reaction mixture at 180° C. for two hours, it is evaporated at 80° to 90° C. on a rotary evaporator and the residue is dissolved in methylene chloride. After washing the organic phase several times with water, the methylene chloride wolution is dried over sodium sulphate and evaporated. The oil which remains is purified by chromatography. (Absorbent: silica gel 60, Merck; solvent: chloroform).

33.2 g (43% of theory) of 2-chlorophenyl-imidazol-1-yl-indan-5-yl-methane of refractive index $n_D^{20}=1.6160$ are obtained.

Preparation of the starting materials

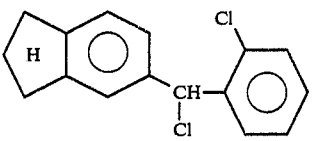

79.3 g (0.26 mol) of 2-chlorophenyl-indan-5-yl-carbinol, dissolved in 150 ml of benzene, are added dropwise to a mixture of 21.5 ml (0.26 mol) of thionyl chloride and 150 ml of benzene at 70° C. After heating the reaction mixture under reflux for five hours, it is evaporated. 71 g (98% of theory) of 2-chlorophenyl-indan-5-yl-chloromethane of refractive index $n_D^{20} = 1.6050$ are obtained.

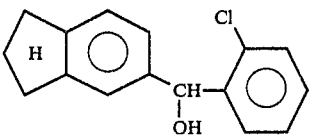

5.7 g (0.15 mol) of sodium boranate are introduced in portions into a solution of 79.6 g (0.3 mol) of 2-chlorophenyl-indan-5-yl ketone in 500 ml of ethyl alcohol. The reaction mixture is warmed to 80° C. for 4 hours and then poured onto ice and extracted with methylene chloride. The organic phase is dried over sodium sulphate and evaporated. 79.3 g (98% of theory) of 2-chlorophenyl-indan-5-yl-carbinol of refractive index $n_D^{20} = 1.6012$ are obtained.

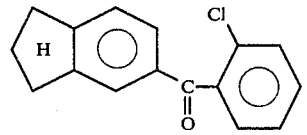

66.7 g (0.5 mol) of aluminium chloride are added in portions to a mixture of 59 g (0.5 mol) of indane, 87.5 g (0.5 mol) of 2-chlorobenzoyl chloride and 200 ml of methylene chloride at room temperature. After the reaction has ended, the mixture is stirred for a further 4 hours and poured onto ice/hydrochloric acid. The organic phase is washed with water until neutral, dried over sodium sulphate and evaporated. The crude product is purified by distillation.

79.6 g (60% of theory) of 2-chlorophenyl indan-5-yl ketone of boiling point 160° C./$_{0.15}$ mm are obtained.

EXAMPLE 3

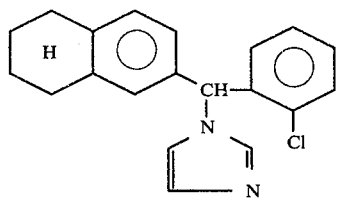

44 g (0.15 mol) of 2-chlorophenyl-1,2,3,4-tetrahydronaphth-6-yl-chloromethane, dissolved in 50 ml of 1,2-dichlorobenzene, are added dropwise to a suspension of 51 g (0.75 mol) of imidazole in 100 ml of 1,2-dichlorobenzene at 180° C. The reaction mixture is heated to 180° C. for 2 hours and, after cooling, is poured onto water and the organic phase is diluted with methylene chloride and washed with water. After drying the solution over sodium sulphate, it is evaporated in vacuo. 26.8 g (55% of theory) of 2-chlorophenyl-imidazol-1-yl-1,2,3,4-tetrahydronaphth-6-yl-methane of refractive index $n_D^{20} = 1.6000$ are obtained.

The compounds in Table 1 which follows are obtained in a corresponding manner.

TABLE 1

| Ex. No. | $R_n$ | $R^1$ | $R^2$ | $R^3m$ | Physical constant |
|---|---|---|---|---|---|
| 4 | — | 3,4-(CH$_2$)$_4$— | | — | $n_D^{20}$ :1.5912 |
| 5 | — | 3,4-(CH$_2$)$_4$— | | 2-CH$_3$ | $n_D^{20}$ :1.6040 |
| 6 | — | 3,4-(CH$_2$)$_4$— | | 4-Cl | $n_D^{20}$ :1.5904 |
| 7 | — | 3,4-(CH$_2$)$_3$— | | — | $n_D^{20}$ :1.5914 |
| 8 | — | 3,4-(CH$_2$)$_3$— | | 2-CH$_3$ | $n_D^{20}$ :1.6018 |
| 9 | — | 3,4-(CH$_3$)$_3$— | | 4-Cl | $n_D^{20}$ :1.6031 |
| 10 | — | 4—⟨H⟩ | H | 2-Cl | Fp:104° C. |
| 11 | — | 3,4-(CH$_2$)$_4$— | | 2-F | $n_D^{20}$ :1.5890 |
| 12 | — | 3,4-(CH$_2$)$_3$— | | 2-F | $n_D^{20}$ :1.6000 |
| 13 | — | 4—⟨H⟩ | H | 2-F | Melting point: 102° C. |
| 14 | — | 4—⟨H⟩ | H | 4-Cl | $n_D^{20}$ :1.5867 |
| 15 | — | 3,4-(CH$_2$)$_3$— | | 2-F | Melting point: 130° C. (× HCl) |
| 16 | — | 3,4-(CH$_2$)$_4$— | | 2-F | Melting point: 175° C. (× HCl) |
| 17 | — | 4—⟨H⟩ | H | 2-F | Melting point: 175–176° C. (× HCl) |
| 18 | — | 4—⟨H⟩ | H | 2,4-Cl$_2$ | $n_D^{20}$ :1.5848 |
| 19 | — | 4—⟨H⟩ | H | 2,5-Cl$_2$ | $n_D^{20}$ :1.5795 |
| 20 | — | 4—⟨H⟩ | H | 2-Br | Melting point: 110° C. |

Among the new substituted diphenyl-imidazolylmethane salts of the invention, those salts that are pharmaceutically acceptable are particularly important and are preferred.

The new free substituted diphenyl-imidazolylmethanes of the general formula I and their salts can be interconverted in any suitable manner; methods for such interconversion are known in the art.

The present invention also comprises pharmaceutically acceptable bioprecursors of the active compounds of the present invention.

For the purposes of this Specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A compound of the formula

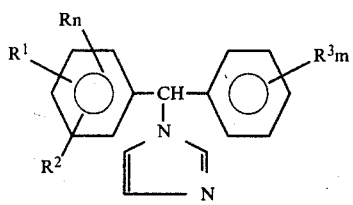

or a pharmaceutically acceptable acid addition salt thereof in which

R denotes a halogen atom or an alkyl or alkoxy group with, in each case, 1 to 4 carbon atoms or a halogenalkyl group with 1 to 4 carbon atoms and up to 5 fluorine or chlorine atoms, $R^1$ denotes a cycloalkyl group with 3 to 7 carbon atoms which is unsubstituted or substituted by fluorine, chlorine, bromine or alkyl with 1 to 4 carbon atoms, $R^2$ denotes a hydrogen atom or $R^1$ and $R^2$, in the ortho-position relative to one another, together denote a multi-membered methylene bridge with 3 to 5 methylene groups which is unsubstituted or substituted by fluorine, chlorine, bromine or alkyl with 1 to 4 carbon atoms, $R^3$ denotes a halogen atom a straight-chain or branched alkyl with 1 to 4 carbon atoms, a halogenoalkyl group with 1 to 4 carbon atoms and up to 5 fluorine or chlorine atoms, an alkoxy, alkylthio or alkylsulphonyl group with 1 to 4 carbon atoms, n and m are independently 0,1,2 or 3, and $R^3$ may also denote cyano when m is 1.

2. A compound according to claim 1, in which R denotes a fluorine, chlorine or bromine atom, a straight-chain or branched alkyl or alkoxy group with in each case 1 to 4 carbon atoms or a halogenoalkyl group with 1 to 4 carbon atoms and up to 5 fluorine or chlorine atoms, R $R^1$ denotes a cycloalkyl group with 3 to 7 carbon atoms which is unsubstituted or substituted by fluorine, chlorine, bromine or alkyl with 1 to 4 carbon atoms, $R^2$ denotes a hydrogen atom or denotes, together with $R^1$, in the ortho-position relative to one another, a methylene bridge with 3 to 5 methylene groups which is unsubstituted or substituted by fluorine, chlorine, bromine or alkyl with 1 to 4 carbon atoms, $R^3$ denotes a fluorine, chlorine or bromine atom, a straight-chain or branched alkyl with 1 to 4 carbon atoms, a halogenoalkyl group with 1 to 4 carbon atoms and up to 5 fluorine or chlorine atoms, an alkoxy, alkylthio or alkylsulphonyl group with 1 to 4 carbon atoms or an amino, nitro or cyano group.

3. A compound according to claim 2, in which R or $R_3$, as a halogenoalkyl group, has 1 or 2 carbon atoms and is substituted by up to 3 identical or different fluorine or chlorine atoms.

4. Phenyl-imidazol-1-yl-1,2,3,4-tetrahydronaphth-6-yl-methane.

5. 4-Chlorophenyl-imidazol-1-yl-1,2,3,4-tetrahydronaphth-6-yl-methane.

6. Phenyl-imidazol-1-yl-indan-5-yl-methane.

7. 4-Chlorophenyl-imidazol-1-yl-indan-5-yl-methane.

8. 4-Chlorophenyl-imidazol-1-yl-4-cyclohexylphenyl-methane.

9. A pharmaceutical composition containing as an active ingredient an antimycotically effective amount of a compound according to claim 1 in admixture with a solid, liquid or liquefied gaseous diluent.

10. A pharmaceutical composition containing as an active ingredient an antimycotically effective amount of a compound according to claim 1 in the form of a sterile or physiologically isotonic aqueous solution.

11. A composition according to claim 9 or 10 containing from 0.5 to 95% by weight of the said active ingredient.

12. A medicament in dosage unit form comprising an antimycotically effective amount of a compound according to claim 1 together with an inert pharmaceutical carrier.

13. A medicament of claim 12 in the form of tablets, pills, dragees, capsules, ampoules, or suppositories.

14. A method of combating mycotic diseases in warm-blooded animals which comprises administering to the animals an antimycotically effective amount of an active compound according to claim 1 either alone or in admixture with a diluent or in the form of a medicament.

15. A method according to claim 14 in which the active compound is administered in an amount of 10 to 300 mg per kg body weight per day.

16. A method according to claim 15 in which the active compound is administered in an amount of 50 to 200 mg per kg body weight per day.

17. A method according to claim 14 in which the active compound is administered parenterally.

* * * * *